US005902937A

United States Patent [19]
Amrani et al.

[11] Patent Number: 5,902,937
[45] Date of Patent: May 11, 1999

[54] IN VITRO TISSUE TESTING SYSTEM

[75] Inventors: David L. Amrani, Glendale, Wis.; Danial R. Boggs, Libertyville; Keith A. Earles, Waukegan, both of Ill.

[73] Assignee: Baxter International Inc., Deerfield, Ill.

[21] Appl. No.: 08/941,994

[22] Filed: Oct. 1, 1997

[51] Int. Cl.⁶ .............................. G01N 3/02; G01N 37/00
[52] U.S. Cl. ................................................ 73/856; 73/64.41
[58] Field of Search ........................ 73/64.41, 64.55, 73/856, 860

[56] References Cited

U.S. PATENT DOCUMENTS

| | | | |
|---|---|---|---|
| 4,864,865 | 9/1989 | Stoakley et al. | 73/860 |
| 4,986,964 | 1/1991 | Carr, Jr. et al. | 73/64.41 |
| 5,289,826 | 3/1994 | Kovacevic | 73/862.634 |
| 5,293,772 | 3/1994 | Carr, Jr. | 73/64.41 |
| 5,777,215 | 7/1998 | Calatzis et al. | 73/64.41 |

OTHER PUBLICATIONS

U.S. Department of Health and Human Services, Public Health Service, National Institutes of Health, "Guidelines for Blood–Material Interactions", Devices and Technology Branch, Division of Heart and Vascular Diseases, National Heart, Lung, and Blood Institute, May. 1979.

*Primary Examiner*—Max H. Noori
*Attorney, Agent, or Firm*—Guy L. Cumberbatch

[57] ABSTRACT

An in vitro tissue testing system especially useful for testing blood/tissue interactions. The system includes a tissue holding frame which forms a chamber between two flat pieces of tissue with a spacer plate therebetween. The spacer plate includes a reservoir aperture bordered on both sides by the opposed tissue pieces, and a mechanism for depressing portions of the tissue pieces inwardly into the chamber to propel blood from one side of the chamber to the other. The flow created simulates actual blood flow in a host system. The reservoir aperture may be hourglass shaped with circular end portions and a middle blood passageway. The actuating mechanism may include pistons for alternating contact with the tissue within the confines of the opposite reservoir end portions, thus propelling blood from one end portion to the other. The pistons may be driven by a plurality of eccentric cams on shafts coupled to a common drive motor. The holding frame may include two outer plates for sandwiching the tissue pieces against the spacer plate, the outer pieces having openings corresponding to the reservoir end portions, and the pistons reciprocate through the openings into contact with the tissue.

28 Claims, 3 Drawing Sheets

IN VITRO TISSUE TESTING SYSTEM

Field of the Invention

The present invention relates generally to an in vitro test system used to evaluate the effects of two surface modifying treatments on pericardial tissue hemocompatibility.

Background of the Invention

Bovine pericardium has been used as a biomaterial for heart valves since the late 1960's. Cross-linking agents have been routinely applied to reduce host-tissue response including antigenicity and improve tissue leaflet durability. Bioprosthetic heart valves are produced from either intact porcine valves or fabricated from pieces of bovine pericardial tissue treated with glutaraldehyde (GA). (See, e.g., Carpentier A, et al., "Biological factors affecting long term results in valvular heterografts", J Thorac Cardiovasc Surg 1969;58:467–83; and Woodroof EA. "Use of glutaraldehyde and formaldehyde to process tissue heart valves" J Bioeng 1978;2:1–4.) Glutaraldehyde treatment, introduced by Carpentier et al., was intended to modify the heterograft collagen and make it immunologically more compatible with the human host. Treatment of valvular tissues with aldehydes prevents degeneration of these biomaterials as well as other tissues. While these treated valves are relatively non-thrombogenic and immunogenic, they have problems related to the interactive chemistry of GA with tissue and host interactions. Moreover, because of the possibility of bioprosthetic tissue calcification and loss of tissue flexibility, rigorous testing of such materials to predict their implanted life is common.

Evaluation of bovine pericardial valve leaflet calcification and flexibility require that in vitro systems be developed to correlate with results from in vivo studies. A number of in vitro and in vivo methods have been developed to assess biocompatibility and calcification. Static exposure to salt solutions, exposure to endothelial cells to determine effect on cell growth, or in vivo implantation into rat subcutaneous pockets or peritoneal cavity are examples of methods for these assessments. Studies to examine the effects of surface modification of bovine pericardial tissue with the intent of modifying the charge or bonds resulting in release of aldehyde moieties are primarily directed at tissue failure due to calcification. In addition, methods such the millipore diffusion chamber subcutaneous implant model suggest that calcification is independent of host cell interaction. The potential role of blood protein/cellular interaction with aldehydealtered or weakened collagen cross-linkages may contribute to these processes.

To rapidly assess the degree of both blood protein and cellular response to modified bovine pericardial tissue (as one means of determining better methods for decreasing calcification), in vitro exposure to whole blood or other biological fluids is regularly performed prior to in vivo studies. Test systems include static and dynamic models, with the dynamic models simulating blood flow past tissue. Flow models typically utilize a blood pump and tubing circuit, with the specimen being tested immersed in the flow. Blood pumps can damage blood, and such flow past tissue does not adequately take into account the fluid forces imposed on implanted tissue, such as heart valve leaflets. Moreover, the systems often expose the blood to far too much foreign surface area other than the tissue being tested.

There is thus a need for a simpler and more effective blood/tissue interaction testing system.

SUMMARY OF THE INVENTION

In a preferred embodiment, the present invention provides an in vitro minicam-driven system for evaluating tissue sections for an acute first-pass exposure to whole blood or any biological fluid interactions.

The present invention provides a fluid/material interaction testing system, comprising: a sheet material holding frame having a pair of outer plates adapted to connect together, a central spacer plate having a peripheral portion defining a reservoir aperture, the outer plates adapted to hold a piece of sheet material against either face of the central spacer plate to define a hollow blood chamber between the facing material pieces and within the reservoir aperture. The plates may each include at least one through hole extending from face to face. The reservoir aperture may include a pair of circular end portions sized the same as the through holes in the outer plates, and a blood passageway joining the two end portions. The system may further include at least one piston positioned to reciprocate in and out of each of the through holes into contact with one of the material pieces and depress the sheet material piece toward the blood chamber. Preferably, there are two through holes in each outer plate and four pistons, wherein the two holes in one outer plate are aligned across the plates with the two holes in the other outer plate. The system desirably includes a drive mechanism for reciprocating the pistons into and out of contact with the material pieces.

The present invention also provides a method of testing fluid/material interaction, comprising: positioning two flat pieces of sheet material on opposite faces of a spacer plate, the spacer plate having a peripheral solid portion surrounding a reservoir aperture; firmly pressing and holding the material pieces against the spacer plate so as to create a sealed inner chamber between the material pieces and defined by the reservoir aperture; filling the inner chamber with fluid; and depressing alternating regions of the material pieces within the boundary of the reservoir aperture to compress the inner chamber and move fluid around in the chamber. The fluid may be blood, and the sheet material may be fixed bovine pericardial tissue.

In another aspect, the present invention provides a fluid/material interaction testing apparatus, comprising: a support; a drive mechanism including opposed pairs of pistons mounted in the support for reciprocal motion toward and away from one another; a sheet material holding frame positioned on the support between the opposed pairs of pistons, the sheet material holding frame having a pair of spaced material pieces defining within a fluid chamber and having outer faces exposed to the pistons, wherein the pistons are actuated to contact and depress the sheet material outer faces and compress the inner chamber at the location of contact. The apparatus may include a pair of shafts each having a pair of eccentric cams mounted for rotation therewith, the pistons being mounted on inner ends of shafts with cam followers mounted on the outer ends and biased into contact with the eccentric cams, wherein rotation of the shafts causes linear reciprocation of the pistons. Further, the apparatus may include a system of belts and pulleys driven by a motor, the system actuating the pistons on opposite sides of the frame in synchronism. Finally, the sheet material holding frame may include a pair of outer plates adapted to connect together, a central spacer plate having a peripheral portion defining a reservoir aperture, the outer plates adapted to hold a piece of sheet material against either face of the central spacer plate to define the inner chamber between the facing material pieces and within the reservoir aperture.

Further objects and advantages of the present invention shall become apparent to those skilled in the art upon reading and understanding the following detailed description of a presently preferred embodiment of the invention.

DESCRIPTION OF THE PREFERRED EMBODIMENTS

The present invention provides a tissue testing system including a cam-driven mini pumping apparatus and a sandwiched design tissue holding frame. The tissue holding frame is mounted between a pair of oppositely reciprocating pistons, the pistons being driven by a motor and belt pulley system. The tissue holding frame includes a pair of openings on opposite sides through which the pistons of the drive system may extend. Tissue is held between the sandwiched parts of the frame, and a fixed volume of blood is contained in between two sheets of tissue. As the pistons reciprocate inward on one side of the tissue testing frame the blood is pushed to the other side, and vice versa. The testing system enables tissue/blood interaction to be examined using a method which simulates blood flow and actual tissue stress conditions in use. It will be understood by those of skill in the art that the present tissue testing system may be used for testing interactions between sheet materials and fluid, and may be used to test bioprosthetic tissue or other types of sheet material, including PVC and non-biological, non-PVC material. The system may also be used to test material/fluid interactions with fluids other than blood, such as plasma or other biological fluids.

Figure 1:
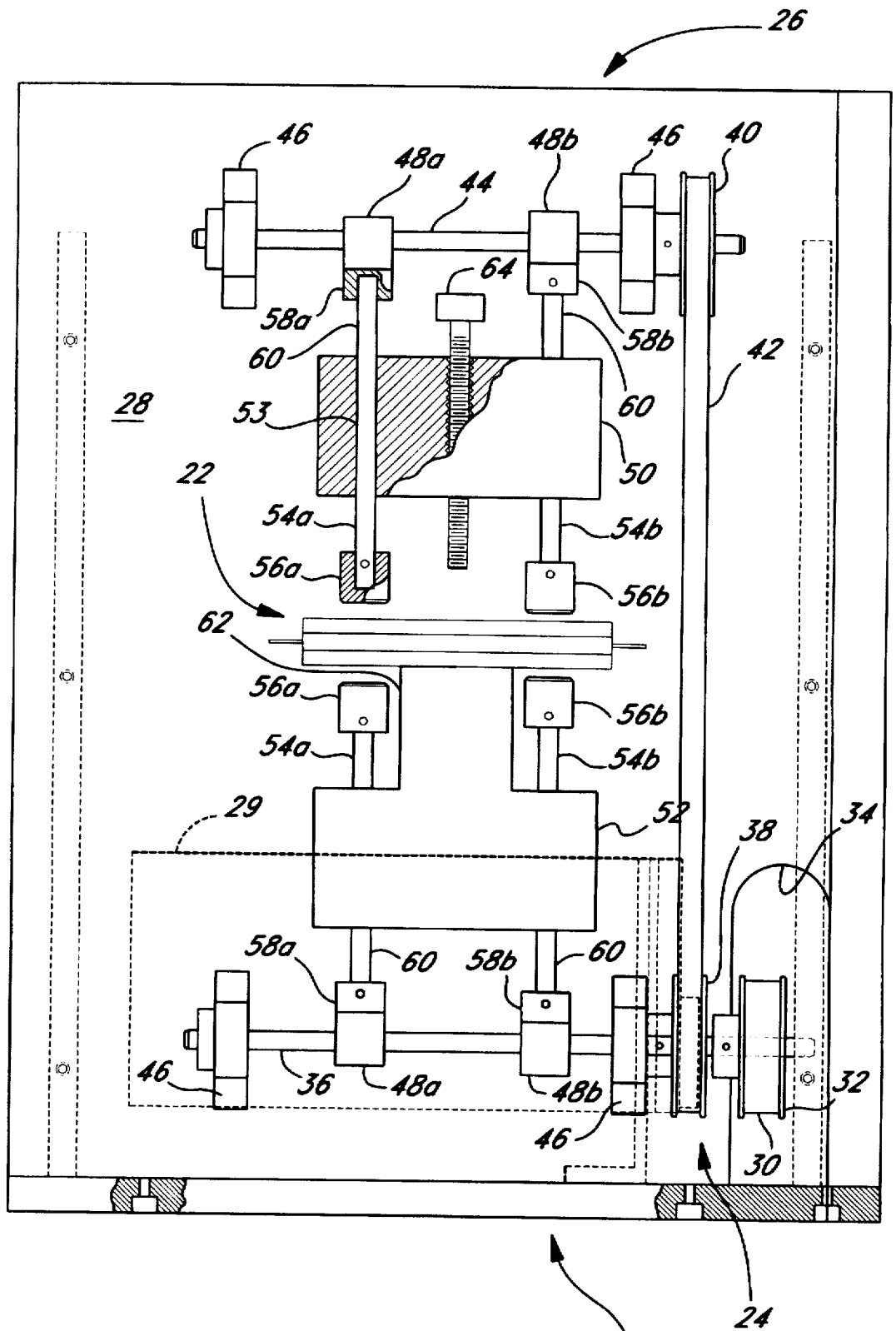
FIG. 1 is an elevational view of a tissue testing system of the present invention.

With reference to FIG. 1, the tissue testing system 20 includes a tissue holding frame 22 and a piston drive mechanism 24. The components of the system 20 are mounted on a fixed support 26, such as a housing constructed of walls of half-inch PVC. Part of the support 26 comprises a front panel 28 behind which a motor 29 (shown in phantom) is provided at a lower end of the system. The motor communicates via a belt 30 with a pulley 32 mounted in front of the panel 28. The belt 30 passes through an aperture 34 in the panel 28. The pulley 32 is keyed to a shaft 36 which, in turn, drives a second pulley 38. The second pulley 38 drives a third pulley 40 via a belt 42 extending substantially the height of the panel 28. The third pulley 40 is also keyed to a shaft 44. The shafts 36 and 44 are mounted for horizontal rotation in front of the panel 28 about a plurality of bearings 46 fixedly mounted to the support 26. A pair of spaced eccentric cams 48a and 48b are mounted on both the lower and upper shafts 36 and 44. As shown in the drawing, a left eccentric cam 48a is mounted both on the lower shaft 36 and the upper shaft 44, and a right eccentric cam 48b is mounted on the two shafts as well. The eccentric cams 48a and 48b are keyed for rotation with the respective shafts 36 and 44.

The horizontal shafts 36 and 44 are spaced apart in front of the panel 28 a vertical distance of approximately 10.2 inches. In between the shafts 36 and 44, an upper linear bearing block 50, and a lower linear bearing block 52 are mounted to the panel 28. Each of the bearing blocks 50 and 52 include vertical through holes 53 for receiving piston shafts 54a and 54b. Each of the shafts 54a and 54b is sized to linearly reciprocate in a region between the tissue holding frame 22 and either the lower shaft 36 or upper shaft 44. In this respect, each of the shafts 54a and 54b includes a piston 56a or 56b mounted on an end facing the tissue holding frame 22. On the end of the shafts 54a and 54b opposite the pistons 56a and 56b, a follower 58a or 58b is mounted. The followers 58a and 58b are biased into contact with the eccentric cams 48a and 48b by a plurality of springs 60 surrounding the shafts 54 and arranged in compression between the followers and the respective linear mounting blocks 50 and 52. Thus, the upper set of shafts 54a and 54b are biased upward, while the lower set of shafts 54a and 54b are biased downward. The tissue holding frame 22 rests on a platform 62 formed as an extension of the lower mounting block 52. In use, a large retaining screw 64 is screwed into contact with the top of the frame 22 to secure it in place.

Figure 2:
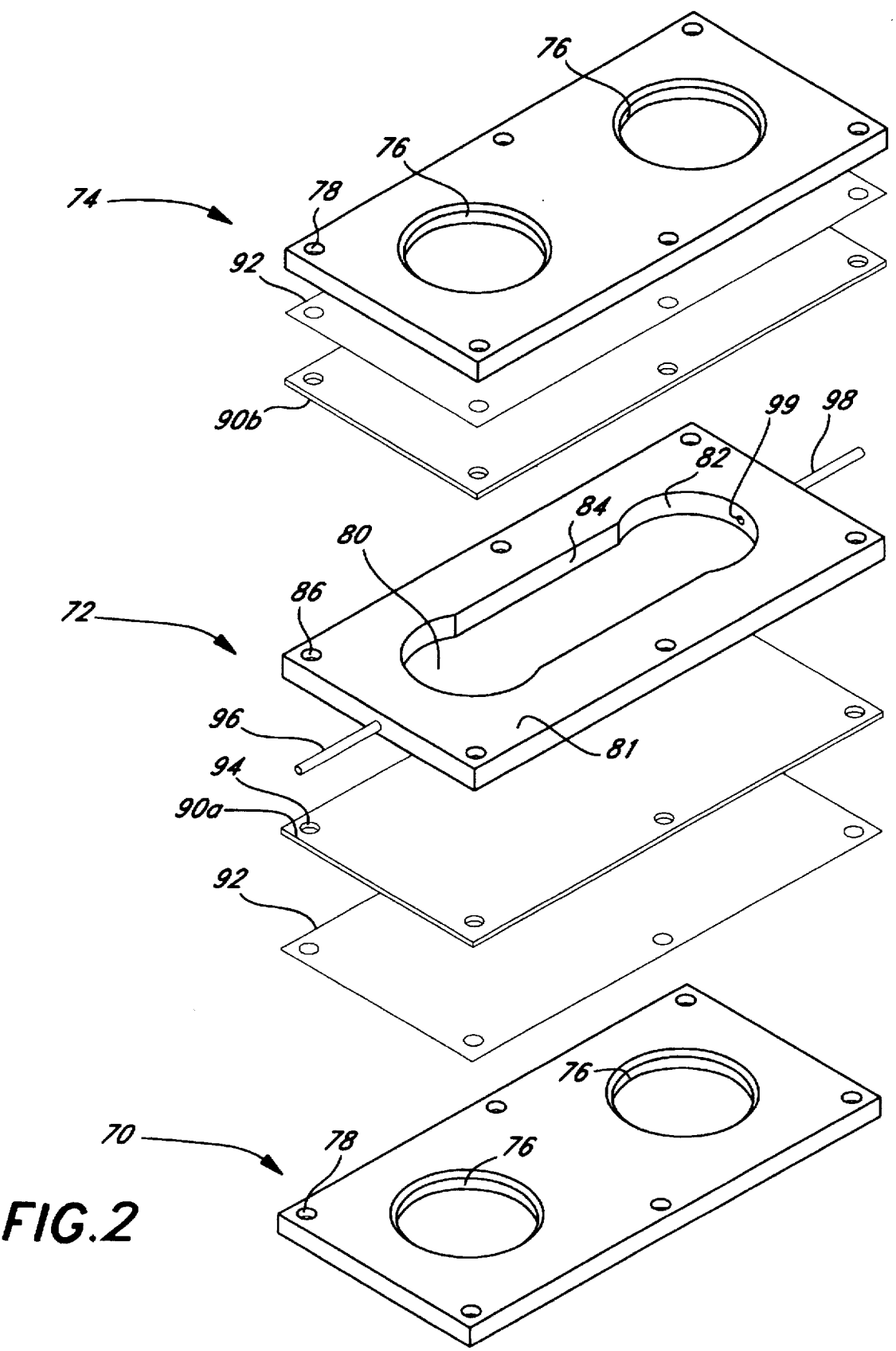
FIG. 2 is a perspective exploded view of a tissue holding frame and tissue pieces for use in the testing system of FIG. 1.

With reference to FIG. 2, the tissue holding frame is shown exploded and comprises a lower plate 70, a center spacer plate 72 and an upper plate 74. In one specific example, each of the plates has a length of 3.5 inches (8.9 cm), a width of 1.5 inch (3.8 cm) and a face-to-face thickness of 0.125 inch (0.318 cm). The lower plate 70 and upper plate 74 are identical and each have a pair of relatively large apertures 76 therethrough. Each of the apertures 76 are chamfered at the circular intersections with the opposite faces of the plates 70 and 74. The plates 70 and 74 further include a plurality of mounting holes 78, preferably six, with the holes on the lower plate being tapped. The spacer plate 72 has a solid peripheral portion 81 with a relatively large, hour-glass shaped reservoir aperture 80 therein from one face to another. The aperture 80 comprises circular end portions 82 having the same size as the circular apertures 76 in the plates 70 and 74, and a central blood passageway 84 joining the circular end portions 82. The spacer plate 72 further includes a plurality of mounting holes 86 which register with the mounting holes in the lower and upper plates 70 and 74. The system is designed to limit exposure of anticoagulated whole blood to only the materials being tested, and the plates 70, 72 and 74 are desirably titanium to reduce interactions with the blood.

Two pieces of tissue 90 are adapted to be held within the sandwiched plates 70, 72 and 74. More particularly, a lower piece of tissue 90a sandwiched between the lower plate 70 and the spacer plate 72, and an upper tissue piece 90b is sandwiched between the center plate and the upper plate 74. Silicone sheet gaskets 92 are placed between each tissue piece 90a and 90b and its respective lower plate 70 and upper plate 74. The gaskets help prevent blood seepage through the tissue pieces 90a or 90b to the outer plates 70 and 74. Desirably, no gasket is placed between the tissue pieces 90 and 90b and the spacer plate 72.. The tissue pieces 90a,b and gaskets 92 include through holes around their edges through which fasteners pass to couple the plates and tissue pieces together.

When the three plates are sandwiched together, they appear as in FIG. 1 with the lower and upper plates 70, 74 outside of the center spacer plate 72. Bolts (not shown) firmly sandwich the assembly of the three plates, tissue pieces and gaskets to prevent blood leakage from a chamber 95 (FIGS. 3a and 3b) formed within the boundary of the reservoir aperture 80 and between opposed faces of the tissue pieces.

An inlet conduit 96 is attached to one short end of the spacer plate 72 and placed in communication with the chamber 95. Likewise, an outlet conduit 98 is attached to the opposite short end of the spacer plate 72 and placed in communication with the chamber 95 through an aperture 99 (FIG. 2) in the peripheral portion 81. Blood may be introduced to the chamber via either conduit 96 or 98, and the conduits closed to form a closed volume chamber 95. The tubing and blood supply system are not shown and are conventional as known in the art. Alternatively, blood may be circulated through the chamber 95 during the testing as desired.

OPERATION

Figure 3A:
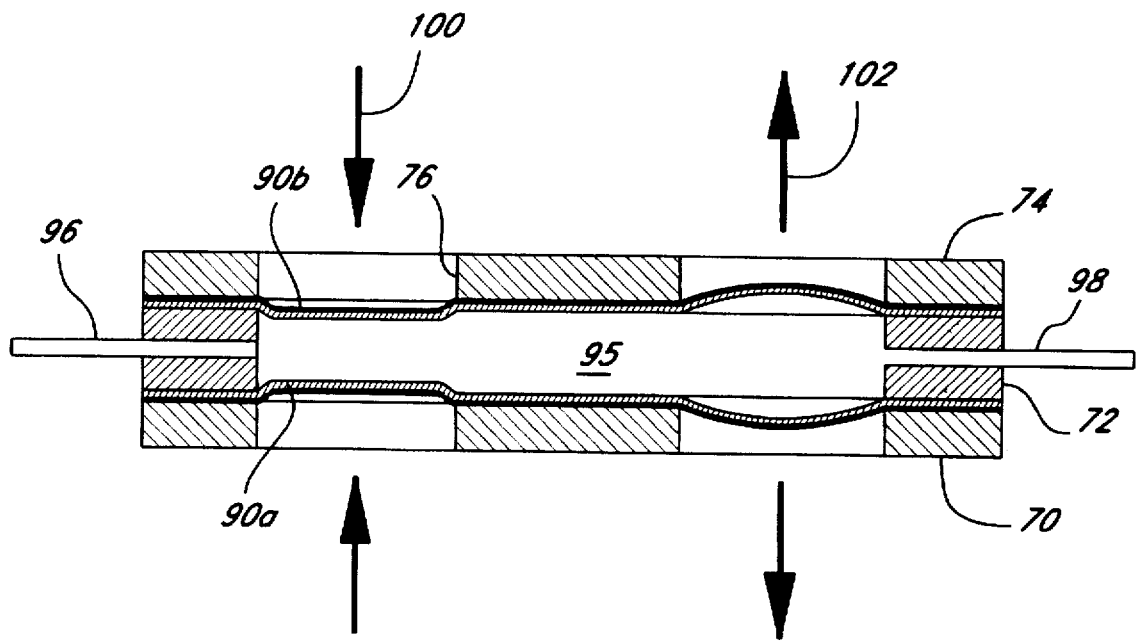
FIG. 3a is a cross-sectional view showing the tissue holding frame and a portion of the testing system in a first operating mode.
Figure 3B:
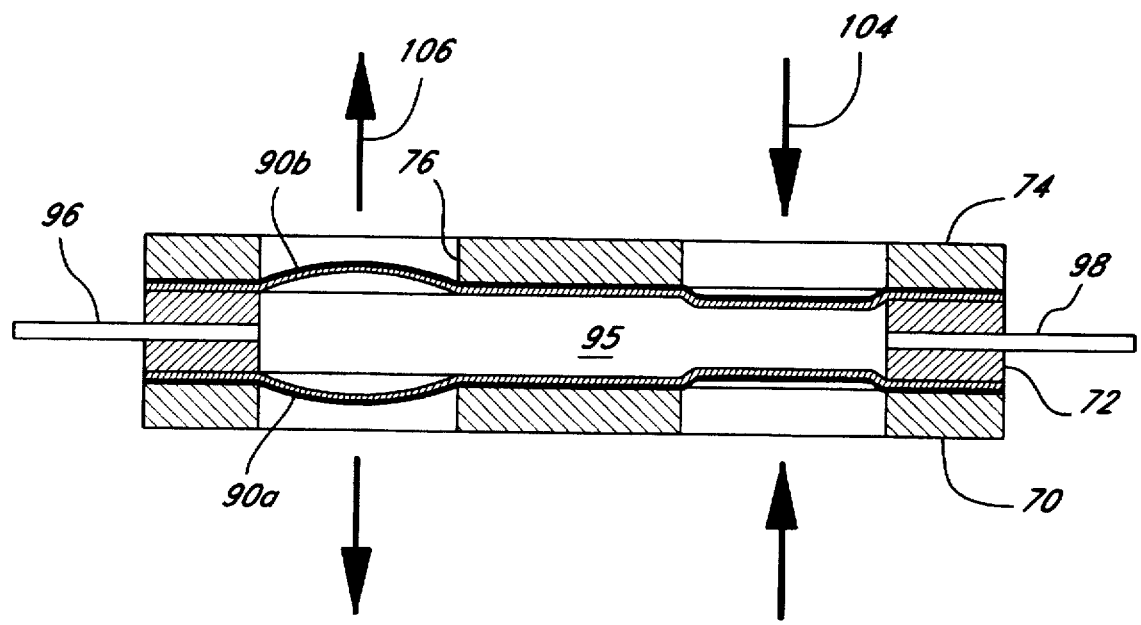
FIG. 3b is a cross-sectional view similar to FIG. 3a with the system in a second operating mode.

The system operates as seen in FIGS. 3a and 3b. After blood has been injected into the hour-glass shaped aperture 80 between the pieces of tissue 90a and 90b, the inlet and outlet conduits 96 and 98 of the spacer plate 72 are closed. The drive mechanism 24 is actuated with the motor 29 turning the various pulleys and belts to rotate the eccentric cams 48a and 48b. As the followers 58a and 58b are biased into contact with the eccentric cams 48a and 48b, they are linearly reciprocated up and down. The eccentric cams are sized and oriented to push the followers 58a toward each other in one phase of operation, as seen schematically by the arrows 100 in FIG. 3a, and push the followers 58b towards one another in a second phase of operation, as seen schematically by the arrows 104 in FIG. 3b. The phases of operation are preferably 180° apart during the rotation of the shafts 36 and 44.

The pistons 56a and 56b contact the tissue through the apertures 76 and press opposed tissue surfaces toward one another in one of the circular end portions 82 of this spacer plate 72. In this way, blood is forced to the left and then to the right within the aperture 80. The shape of the aperture 80 is such that no stasis of blood occurs and the blood is continuously flushed from one end of the reservoir to the other. As blood is flushed to one end, the tissue at that end bulges outward as seen schematically by the arrows 102 and 106 in FIGS. 3a and 3b. This bulging creates a stress in the tissue which more closely simulates the stress imposed on implanted tissue than in previous devices. More particularly, the tissue is stressed in both directions which closely simulates the actual stresses imposed on heart valve leaflets. Further, the reservoir aperture 80 is shaped such that a constant flushing of the inner chamber 95 occurs, leaving no areas of stagnation. The pistons 56 are sized the same as the end portions 82, and so the entire end of the chamber 95 is compressed to push blood to the other end, and visa versa.

In one particular example of a test regimen, two glutaraldehyde (GA) treated pieces of pericardial tissue were used in these studies of the devised in vitro test system. Tissue sections (1.5×3.5 inches) were evaluated in a the chamber 95. The chamber 95 desirably has a total volume of approximately 7 ml. The design will allow for the flow of liquid across the tissue surfaces with minimal contact with the titanium surfaces of the frame structure. The two short sections of titanium conduit, one at either end, allow for the introduction of fluids and provide for sampling sites. As one side of the cam-driven set of pistons move away from the tissue surface the other side presses on the tissue and forces movement of the blood into the circular portions of the upper and lower parts of the chamber as well as across the tissue surfaces which results in no areas of stasis.

Actual studies were conducted as follows: 30 ml of anticoagulated blood was obtained by butterfly needle venous puncture and syringe draw from healthy human donors with informed consent of Baxter IRB and anticoagulated with citrate phosphate dextrose solution (Baxter Healthcare Corp.) containing 50 U/ml Hirudin (Sigma Chemical Co., cat., H-7016) final concentration. The initial 2–3 ml drawn were discarded. The pericardial tissue was secured in the test chamber holder (FIG. 1) and 7 ml whole blood was introduced via the side port. The holder was inserted into the test chamber and secured (FIG. 2). The pump was turned on and the system was allowed to operate for one hour at room temperature. At the conclusion, the pump was turned off and the blood was drained into a polypropylene test tube containing prostaglandin E1 (Sigma Chemical Co., cat.# P-5515) and theophylline (Sigma Chemical Co., cat.# T-1633) at final concentrations of 1 µg/ml and 5.4 µg/ml, respectively. The test tube was placed on ice for at least 10 minutes and then centrifuged at 3500×g for ten minutes to produce Platelet Poor Plasma (PPP). In addition, control blood samples were prepared: a) not exposed to tissue remaining in the whole blood after initial draw (pre sample) and b) at the conclusion of the last experiment of the day (post sample. The PPP was then frozen at −80° C. until analyzed. This procedure was followed for an n=4 for both GA-treatment methods.

It is understood that the examples and embodiments described herein and shown in the drawings represent only the presently preferred embodiments of the invention, and are not intended to exhaustively describe in detail all possible embodiments in which the invention may take physical form. Indeed, various modifications and additions may be made to such embodiments without departing from the spirit and scope of the invention.

What is claimed is:

1. A fluid/material interaction testing system, comprising: a sheet material holding frame having a pair of outer plates adapted to connect together, a central spacer plate having a peripheral portion defining a reservoir aperture, the outer plates adapted to hold a piece of sheet material against either face of the central spacer plate to define a hollow blood chamber between the facing material pieces and within the reservoir aperture.

2. The system of claim 1, wherein the plates each include at least one through hole extending from face to face.

3. The system of claim 2, wherein the reservoir aperture includes a pair of circular end portions sized the same as the through holes in the outer plates, and a blood passageway joining the two end portions.

4. The system of claim 2, further including at least one piston positioned to reciprocate in and out of each of the through holes into contact with one of the material pieces and depress the sheet material piece toward the blood chamber.

5. The system of claim 4, wherein there are two through holes in each outer plate and four pistons, and wherein the two holes in one outer plate are aligned across the plates with the two holes in the other outer plate.

6. The system of claim 5, further including a drive mechanism for reciprocating the pistons into and out of contact with the material pieces.

7. The system of claim 6, wherein the drive mechanism includes a pair of shafts each having a pair of eccentric cams, each eccentric adapted to reciprocate the pistons into and out of contact with the material pieces, the eccentric cams being disposed to drive two aligned pistons one both sides of the sheet material holding frame into contact with the material pieces at the same time, while the other two aligned pistons are retracted.

8. The system of claim 2, wherein the reservoir aperture includes a pair of circular end portions sized the same as the through holes in the outer plates, and a blood passageway joining the two end portions, the system further including at least one piston positioned to reciprocate in and out of each of the through holes into contact with one of the material pieces and depress the sheet material piece toward the blood chamber.

9. The system of claim 1, wherein the outer plates and spacer plate are titanium.

10. The system of claim 1, further including a gasket positioned between each of the outer plates and one of the material pieces, the gaskets being sized larger than the reservoir aperture.

11. The system of claim 1, further including a blood inlet conduit and a blood outlet conduit provided in the spacer plate, both in communication with the blood chamber.

12. A method of testing fluid/material interaction, comprising:

positioning two flat pieces of sheet material on opposite faces of a spacer plate, the spacer plate having a peripheral solid portion surrounding a reservoir aperture;

firmly pressing and holding the material pieces against the spacer plate so as to create a sealed inner chamber between the material pieces and defined by the reservoir aperture;

filling the inner chamber with fluid; and depressing alternating regions of the material pieces within the boundary of the reservoir aperture to compress the inner chamber and move fluid around in the chamber.

13. The method of claim 12, wherein the fluid is blood.

14. The method of claim 13, wherein the sheet material is fixed biological tissue.

15. The method of claim 14, wherein the tissue is fixed bovine pericardial tissue.

16. The method of claim 12, wherein the step of firmly pressing and holding is accomplished by sandwiching the spacer plate between two outer plates of approximately the same exterior dimensions as the spacer plate.

17. The method of claim 16, further comprising positioning a gasket between each outer plate and a sheet material piece.

18. The method of claim 16, wherein the two outer plates each include at least one through hole aligned with the reservoir aperture of the spacer plate, and the step of depressing comprises mechanically contacting the material pieces through the holes.

19. The method of claim 18, wherein the step of mechanically contacting the material pieces through the holes is accomplished with pistons actuated with a common drive mechanism.

20. The method of claim 19, wherein there are two through holes in each end of each outer plate, each through hole being aligned with a through hole in the other outer plate, and two pistons on each side of the sheet material holding frame in registry with the two holes, wherein pistons on opposite sides of the frame are actuated in tandem to compress one region of the inner chamber at a time.

21. A fluid/material interaction testing apparatus, comprising:

a support;

a drive mechanism including opposed pairs of pistons mounted in the support for reciprocal motion toward and away from one another;

a sheet material holding frame positioned on the support between the opposed pairs of pistons, the sheet material holding frame having a pair of spaced material pieces defining within a fluid chamber and having outer faces exposed to the pistons, wherein the pistons are actuated to contact and depress the sheet material outer faces and compress the inner chamber at the location of contact.

22. The apparatus of claim 21, including a pair of shafts each having a pair of eccentric cams mounted for rotation therewith, the pistons being mounted on inner ends of shafts with cam followers mounted on the outer ends and biased into contact with the eccentric cams, wherein rotation of the shafts causes linear reciprocation of the pistons.

23. The apparatus of claim 22, including a system of belts and pulleys driven by a motor, the system actuating the pistons on opposite sides of the frame in synchronism.

24. The apparatus of claim 22, wherein the sheet material holding frame includes a pair of outer plates adapted to connect together, a central spacer plate having a peripheral portion defining a reservoir aperture, the outer plates adapted to hold a piece of sheet material against either face of the central spacer plate to define the inner chamber between the facing material pieces and within the reservoir aperture.

25. The system of claim 24, wherein the plates each include two through holes extending from face to face.

26. The system of claim 25, wherein the reservoir aperture includes a pair of circular end portions sized the same as the through holes in the outer plates, and a fluid passageway joining the two end portions.

27. The system of claim 26, wherein the pistons are positioned to reciprocate in and out of each of the through holes into contact with one of the material pieces.

28. The system of claim 27, wherein the two holes in one outer plate are aligned across the plates with the two holes in the other outer plate, and wherein the drive mechanism actuates two pistons on opposite sides of the frame in tandem to compress one region of the inner chamber at a time.

* * * * *